US00PP11161P

United States Patent [19]

Evers

[11] Patent Number: Plant 11,161

[45] Date of Patent: Dec. 21, 1999

[54] HYBRID TEA ROSE PLANT NAMED 'TANNOLLIPA'

[75] Inventor: Hans-Jürgen Evers, Uetersen, Germany

[73] Assignee: Bear Creek Gardens, Inc., Medford, Oreg.

[21] Appl. No.: 08/961,613

[22] Filed: Oct. 31, 1997

[51] Int. Cl.[6] ..... A01H 5/00

[52] U.S. Cl. ..... Plt./134

[58] Field of Search ..... Plt./15, 134

*Primary Examiner*—Howard J. Locker

*Attorney, Agent, or Firm*—Klarquist Sparkman Campbell Leigh & Whinston, LLP

[57] ABSTRACT

A hybrid tea rose plant having distinctive yellow flower buds; bright yellow, large, open flowers on long stems, and good cut flower production.

1 Drawing Sheet

The present invention relates to a new and distinct variety of rose plant of the hybrid tea class which was originated by me by crossing an unnamed seedling, with the variety TANilyks, U.S. Plant Pat. No. 9,065.

The primary objective of this breeding was to produce a new rose variety having the deep yellow flower color and large flower size of the unnamed parent, combined with the very good cut flower production and long stems of the TANilyks parent. The objective was substantially achieved, along with other desirable improvements, as evidenced by the following unique combination of characteristics that are outstanding in the new variety and that distinguish it from its parents, as well as from all other varieties of which I am aware.

1. Distinctive, deep yellow-orange bud and bright yellow flower;
2. Good cut flower production;
3. Long, straight stems;
4. Large, open flower;
5. Production of many, seven-leaflet leaves.

TANnollipa is a cut flower, greenhouse produced rose. Its production is 22–24 stems per plant per year with long, strong stems. It has long buds and excellent color of buds and flowers.

Asexual reproduction of this new variety by budding, as performed at Uetersen, Germany, and at Wasco, Calif., shows that the foregoing and all other characteristics and distinctions come true to form and are established and transmitted through succeeding propagation.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—TANilyks (U.S. Plant Pat. No. 9,065).

Classification:

*Botanical.*—Rosa hybrida.

*Commercial.*—Hybrid tea.

FLOWER

Observations made from specimens grown in a greenhouse environment at Uetersen, Germany, and at Somis, Calif. from December, 1995 to June, 1996.

Blooming habit: Continuous.

Bud:

*Size.*—Two inches long when the petals start to unfurl.

*Form.*—The bud form is long, pointed ovoid.

*Color.*—When sepals first divide, bud color is Yellow-orange Group 23A, with a green (Green Group 138B) streak along the petal midrib. When half blown, the upper sides of the petals are Yellow Group 13B; and the lower sides of the petals are Yellow Group 13B.

*Sepals.*—Color: Green group 138B. Surface texture: Covered in fine hairs. There are three normally appendaged sepals. There are two unappendaged sepals with hairy edges.

*Receptacle.*—Color: Green Group 143C. Shape:Funnel. Size: Small (⅜" long×⅜" wide). Surface: Smooth.

*Peduncle.*—Length: Medium (3"). Surface: Smooth. Color: Medium green (Green Group 137D). Strength: Stiff, erect, heavy.

Bloom:

*Size.*—Large. Average open size is 4½ inches.

*Borne.*—Singly.

*Stems.*—Long (24"–28"), strong.

*Form.*—When first open: High centered. Permanence: Flattens; all petals curl; some quilling.

*Petalage.*—Number of petals under normal conditions: 30.

*Color.*—The upper sides of the petals are Yellow Group 13B. The reverse sides of the petals are Yellow Group 13B. The base of each petal has a small area at its base (1/16"×1/16"), very deep yellow. The major color on the upper sides is Yellow Group 13B.

*Variegations.*—Green (Green Group 138B) streaks (upper and lower surfaces) on mid ribs of guard petals.

*Discoloration.*—The general tonality at the end of the first day: No change. At the end of the third day: Little change. By day 6 or 7 in the vase, there is some fading of color to Yellow Group 13C.

*Fragrance.*—Moderate.

Petals:

*Texture.*—Thick.

*Shape.*—Round.

*Form.*—Tips slightly recurved.

*Arrangement.*—Imbricated with few (0–4) petaloids of Yellow Group 13B in the center, averaging 20 mm in length and 7 mm in width.

*Persistence.*—Drop off cleanly.

*Lastingness.*—On the plant: Long (6–7 days). As a cut flower: Long (10–12 days).

Reproductive Parts:

*Anthers.*—Size: Large. Quantity: Many. Color: Yellow. Arrangement: Regular around styles, mixed with occasional petaloids.

*Filaments.*—Color: Yellow.

*Pollen.*—Color: Gold yellow.

*Styles.*—Color: Reddish.

*Stigmas.*—Color: Greenish white.

Plant:

*Form.*—Bush.

*Growth.*—Very vigorous; upright; branching. At one year in the greenhouse under traditional cultivation, a plant will be 6–7 feet tall and 4 feet wide.

*Foliage.*—Number of leaflets on normal mid-stem leaves: 5 or 7.

*Size.*—Large (7" long×5½" wide).

*Quantity.*—Abundant.

*Color.*—New foliage: Greyed orange Group 172B on both surfaces. Old foliage: Upper: Green Group 139A. Lower: Green Group 139C.

*Shape.*—Pointed oval.

*Texture.*—Upper side: Leathery.

*Edge.*—Serrated.

*Serration.*—Single, small.

*Petiole rachis.*—Color: Green.

*Petiole underside.*—Rough, with prickles.

*Stipules.*—Long (¾"); serrated, bearded.

*Disease resistance.*—Susceptible to mildew under normal growing conditions at Somis, Calif. Not tested for other diseases.

Wood:

*New wood.*—Color: Green Group 137D. Bark: Smooth.

*Old wood.*—Color: Green Group 137A. Bark: Smooth.

Prickles:

*Quantity.*—On main canes from base: Many. On laterals from main canes: Many.

*Form.*—Long (½"); hooked downward.

*Color when young.*—Greyed Orange Group 176C changing to Greyed Orange Group 173C as plant matures.

Small prickles:

*Quantity.*—On main stalks: None. On laterals: None.

I claim:

1. A new and distinct variety of rose plant of the hybrid tea class, substantially as herein shown and described, characterized particularly as to novelty by its distinctive yellow orange bud; its bright yellow, large, open flower; its good cut flower production with flowers borne on long stems; and its many seven leaflet leaves.

* * * * *

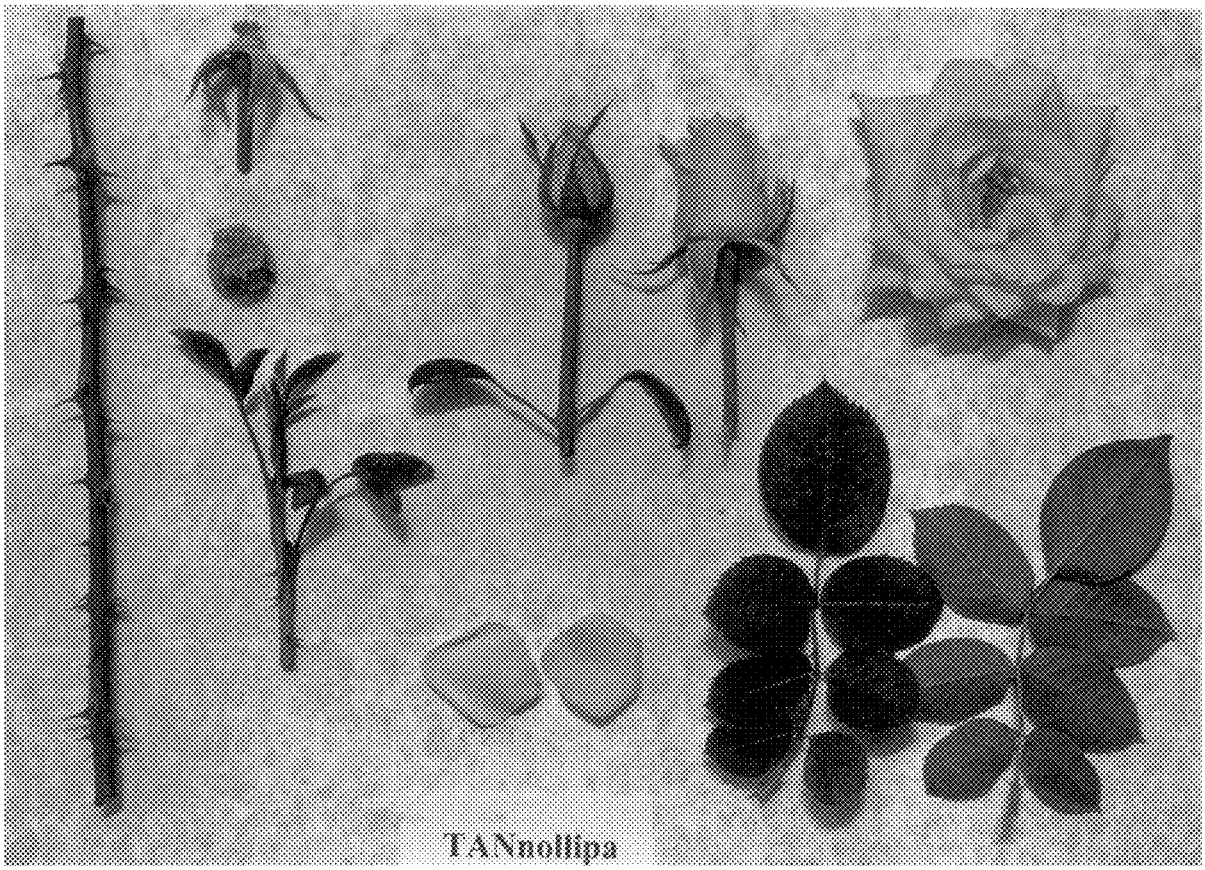
TANnollipa